(12) United States Patent
Huang

(10) Patent No.: US 7,115,411 B2
(45) Date of Patent: Oct. 3, 2006

(54) BACTERIAL STRAIN FOR DEGRADATION OF ORGANIC POLYMERS

(75) Inventor: Shir-Ly Huang, Jungli (TW)

(73) Assignee: National Central University, Taoyuan (TW)

(*) Notice: Subject to any disclaimer, the term of this patent is extended or adjusted under 35 U.S.C. 154(b) by 0 days.

(21) Appl. No.: 10/875,006

(22) Filed: Jun. 22, 2004

(65) Prior Publication Data
US 2005/0063963 A1 Mar. 24, 2005

(30) Foreign Application Priority Data
Sep. 24, 2003 (TW) .............................. 92126305 A

(51) Int. Cl.
*C12N 1/20* (2006.01)

(52) U.S. Cl. ................ 435/253.3; 435/243; 435/252.1; 435/262.5

(58) Field of Classification Search ................ 435/243, 435/248, 249, 253.3, 262
See application file for complete search history.

(56) References Cited

OTHER PUBLICATIONS

Tanghe et al, Applied and Environmental Microbiology, Feb. 1999, vol. 65, No. 2, pp. 746-751.*
Iizuka et al, Journal of General Applied Microbiology, 1964, vol. 10, No. 3, pp. 207-221.*
Maki et al, Applied and Environmental Microbiology, Jul. 1994, vol. 60, No. 7, pp. 2265-2271.*
Sato et al, Polymer Degradation and Stability, 2001, vol. 74, pp. 69-75.*
"Isolation of Bacterial Strains that Produce the Endocrine Disruptor, Octylphenol Diethoxylates, in Paddy Fields" Eriko Nishio et al. / Bioscience, biotechnology, and biochemistry, 2002; 66(9), pp. 1792-1798.

* cited by examiner

*Primary Examiner*—Leon B. Lankford, Jr.
*Assistant Examiner*—Allison M. Ford
(74) *Attorney, Agent, or Firm*—J.C. Patents

(57) ABSTRACT

A Gram-negative bacterial strain, *Pseudomonas nitroreducens* TX1 (BCRC910228) isolated from the surfactant-contaminated drainage sediment is described. This strain is shown to have the capacity in utilizing alkylphenol polyethoxylates as a sole source of carbon and energy to grow. Furthermore, it can be grown on a high concentration of alkylphenol polyethoxylates in an aqueous environment. This strain can be applied in the remediation of organic polymers-contaminated water and soil.

9 Claims, 3 Drawing Sheets

```
          10         20         30         40         50         60
GGCCTAACCA TGCAAGTCGA GCGGATGAGT GGAGCTTGCT CCATGATTCA GCGGCGGACG
          70         80         90        100        110        120
GGTGAGTAAT GCCTAGGAAT CTGCCTGGTA GTGGGGGACA ACGTTTCGAA AGGAACGCTA
         130        140        150        160        170        180
ATACCGCATA CGTCCTACGG GAGAAAGCAG GGGACCTTCG GGCCTTGCGC TATCAGATGA
         190        200        210        220        230        240
GCCTAGGTCG GATTAGCTAG TTGGTGGGGT AAAGGCCTAC CAAGGCGACG ATCCGTAACT
         250        260        270        280        290        300
GGTCTGAGAG GATGATCAGT CACACTGGAA CTGAGACACG GTCCAGACTC CTACGGGAGG
         310        320        330        340        350        360
CAGCAGTGGG GAATATTGGA CAATGGGCGA AAGCCTGATC CAGCCATGCC GCGTGTGTGA
         370        380        390        400        410        420
AGAAGGTCTT CGGATTGTAA AGCACTTTAA GTTGGGAGGA AGGGCAGTAA GTTAATACCT
         430        440        450        460        470        480
TGCTGTTTTG ACGTTACCAA CAGAATAAGC ACCGGCTAAC TTCGTGCCAG CAGCCGCGGT
         490        500        510        520        530        540
AATACGAAGG GTGCAAGCGT TAATCGGAAT TACTGGGCGT AAAGCGCGCG TAGGTGGTTT
         550        560        570        580        590        600
GGTAAGATGG ATGTGAAATC CCCGGGCTCA ACCTGGGAAC TGCATCCATA ACTGCCTGAC
         610        620        630        640        650        660
TAGAGTACGG TAGAGGGTGG TGGAATTTCC TGTGTAGCGG TGAAATGCGT AGATATAGGA
         670        680        690        700        710        720
AGGAACACCA GTGGCGAAGG CGACCACCTG GACTGATACT GACACTGAGG TGCGAAAGCG
         730        740        750        760        770        780
TGGGGAGCAA ACAGGATTAG ATACCCTGGT AGTCCACGCC GTAAACGATG TCGACTAGCC
         790        800        810        820        830        840
GTTGGGATCC TTGAGATCTT AGTGGCGCAG CTAACGCGAT AAGTCGACCG CCTGGGGAGT
         850        860        870        880        890        900
ACGGCCGCAA GGTTAAAACT CAAATGAATT GACGGGGGCC CGCACAAGCG GTGGAGCATG
         910        920        930        940        950        960
TGGTTTAATT CGAAGCAACG CGAAGAACCT TACCTGGCCT TGACATGTCC GGAACCTTGC
         970        980        990       1000       1010       1020
AGAGATGCGA GGGTGCCTTC GGGAATCGGA ACACAGGTGC TGCATGGCTG TCGTCAGCTC
        1030       1040       1050       1060       1070       1080
GTGTCGTGAG ATGTTGGGTT AAGTCCCGTA ACGAGCGCAA CCCTTGTCCT TAGTTACCAG
        1090       1100       1110       1120       1130       1140
CACCTCGGGT GGGCACTCTA AGGAGACTGC CGGTGACAAA CCGGAGGAAG GTGGGGATGA
        1150       1160       1170       1180       1190       1200
CGTCAAGTCA TCATGGCCCT TACGGCCAGG GCTACACACG TGCTACAATG GTCGGTACAG
        1210       1220       1230       1240       1250       1260
AGGGTTGCCA AGCCGCGAGG TGGAGCTAAT CCCATAAAAC CGATCGTAGT CCGGATCGCA
        1270       1280       1290       1300       1310       1320
GTCTGCAACT CGACTGCGTG AAGTCGGAAT CGCTAGTAAT CGTGAATCAG AATGTCACGG
        1330       1340       1350       1360       1370       1380
TGAATACGTT CCCGGGCCTT GTACACACCG CCCGTCACAC CATGGGAGTG GGTTGCTCCA
        1390       1400       1410       1420
GAAGTAGCTA GTCTAACCGC AAGGGGGACG GTACCACGGA
```

BACTERIAL STRAIN FOR DEGRADATION OF ORGANIC POLYMERS

CROSS-REFERENCE TO RELATED APPLICATION

This application claims the priority benefit of Taiwan application serial no. 92126305, filed Sep. 24, 2003.

BACKGROUND OF THE INVENTION

1. Field of the Invention

The present invention relates to a bacterial strain. More particularly, the present invention relates to a bacterial strain capable of degrading organic polymers.

2. Description of Related Art

Currently, organic polymers are extensively used in various manufacturing industries and the agricultural industry. Nonionic surfactants, for example, alkylphenol polyethoxylates, are one type of organic polymers that has been widely used. Alkylphenol polyethoxylates includes nonylphenol polyethoxylates ($NPEO_n$) and octylphenol polyethoxylates ($OPEO_n$). Some of the metabolites from the alkylphenol polyethoxylates type of nonionic surfactants are potential endocrine disrupters and tend to accumulate in the environment, thus ecology and human health can be adversely affected. Consequently, environmental pollution related to the alkylphenol polyethoxylates type of nonionic surfactants has gained a great deal of attention in recent years.

Since the water and soil of many places in the world have been seriously polluted by nonionic surfactants, bioremediation of soil and water contaminated with such nonionic surfactants requires urgent attention. Furthermore, in the bioremediation of petroleum and petrochemical contamination, external surfactants are added to enhance biodegradability. To prevent further contamination during the bioremediation process, the removal of such surfactants is crucial.

SUMMARY OF THE INVENTION

Accordingly, the present invention provides a bacterial strain useful in degrading nonionic surfactants. The bacterial strain of the present invention is able to degrade alkylphenol polyethoxylates type of nonionic surfactants in soil and in water in order to mitigate their environmental pollution problems.

The present invention provides a bacterial strain useful for the degradation of such organic polymers. The bacterial strain of the invention is deposited to Bioresources Collection and Research Center, Food Industry Research and Development Institute of Republic of China (Taiwan), the depository number is BCRC910228. The bacterial strain is a Gram-negative rod-shaped bacterium, isolated from a surfactant-contaminated drainage sediment. This strain demonstrates, under the proper culturing condition, the capacity to degrade alkylphenol polyethoxylates and to use alkylphenol polyethoxylates as a sole source of carbon and energy. Moreover, this bacterial strain can be grown on a high concentration of alkylphenol polyethoxylates in an aqueous environment.

Since the bacterial strain of the invention can effectively degrade alkylphenol polyethoxylates, it is potentially applicable to the bioremediation of water and soils that are contaminated by nonionic surfactants.

It is to be understood that both the foregoing general description and the following detailed description are exemplary, and thus are intended to provide further explanation of the invention as claimed.

A deposit of the biological material has been made on Aug. 26, 2004 at ATCC (American Type Culture Collection), 10801 University Blvd., Manassas, Va. 20110-2209, USA with an accession number PTA-6168. The biological material is a Gram-negative, rod shaped bacterium *Pseudomonas nitroreducens* TX1.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

FIG. 2 is the 16S rDNA sequence of the bacterium of the present invention.

DESCRIPTION OF THE PREFERRED EMBODIMENTS

Figure 1:
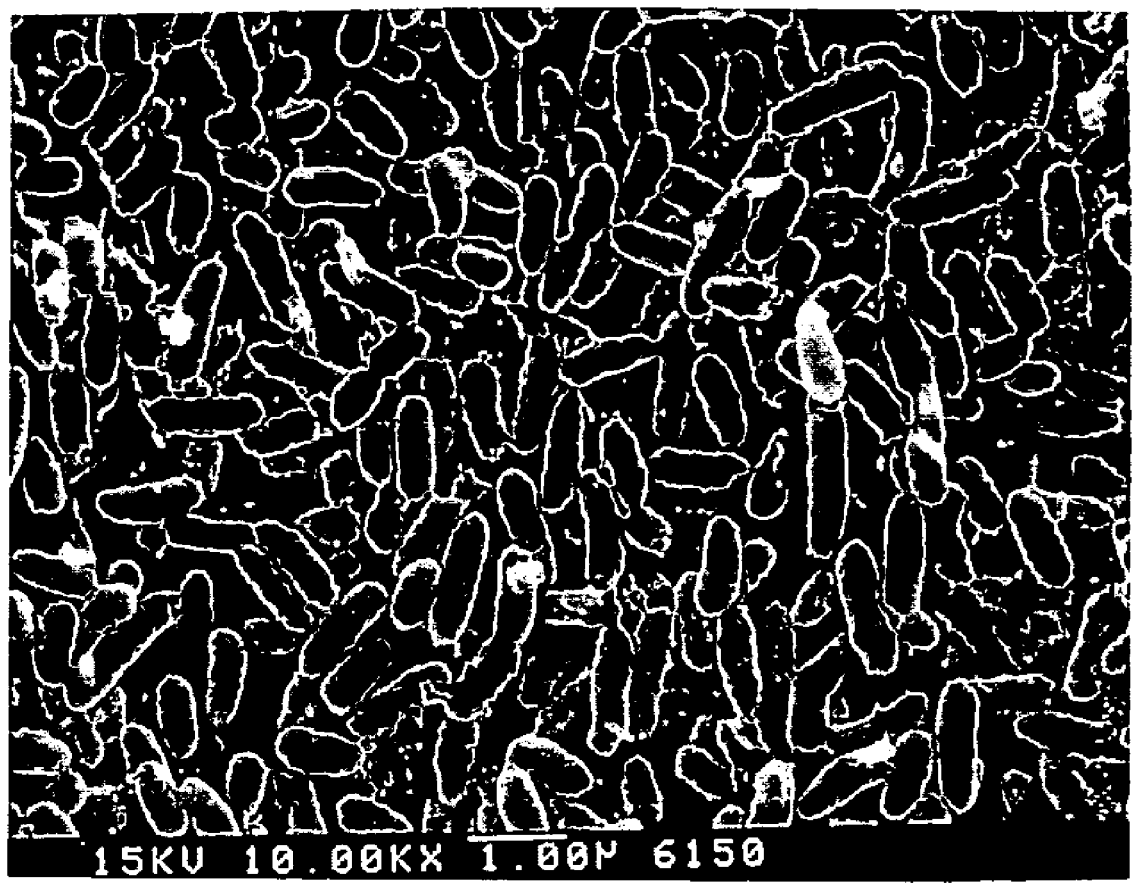
FIG. 1 is a Scanning electron microscope picture of the bacterium of the present invention.

The present invention provides a bacterial strain useful in degrading organic polymer. The bacterial strain of the invention is deposited to Bioresources Collection and Research Center, Food Industry Research and Development Institute of Republic of China (Taiwan), and the depository number is BCRC910228. The bacterial strain is a Gram-negative, rod-shaped bacterium. FIG. 1 is a scanning electron microscope picture of the bacterium of the present invention.

The bacterial strain was isolated from the surfactant-contaminated drainage sediment. The screening method was conducted using enrichment culture. The bacterial strain of the present invention has a variety of biochemical characteristics and these are detailed in the following.

Currently, the bacterial strains best known to have the capability to degrade alkylphenol polyethoxylates type of nonionic surfactants are mainly of the species *Pseudomonas putida*. The bacterial strain of the present invention, after being evaluated by three different methods, is verified to be different from previous published bacterial strains. The bacterial strain of the present invention was confirmed as different by three different methods made up of the 16S rDNA sequencing method, the Biolog method, and the fatty acid fingerprinting method. FIG. 2 is the 16S rDNA sequence of the bacterium of the present invention, referred as SEQ ID NO. 1. The analysis result from the 16S rDNA sequencing method only suggests the bacterial strain of the invention is similar to *Pseudomonas* species. However, the analysis results from the Biolog method suggests that the bacterial strain of the present invention is highly similar to *Pseudornonas nitroreducens*. On the other hand, the analysis result from the fatty acid fingerprinting method suggests that the bacterial strain of the invention is more similar to *Pseudomonas aeruginosa*. Comparing the taxonomic specific biochemical characteristics between *Pseudomnonas aeruginosa* and *Pseudomonas nitroreducens*, gelatin hydrolysis activity is present in *Pseudomonas aeruginosa*, while such an activity is absent in *Pseudomonas nitroreducens*. Thus, based on these biological characteristics, the bacterial strain of the invention is *Pseudomonas nitroreducens*. Since the bacterial strain is shown to have the capacity to utilize Triton X-100 (an OPEOn, when average n=9.5) as a sole source of carbon, it is also known as *Pseudomonas nitroreducens* TX1.

*Pseudomonas nitroreducens* TX1 of the present invention can degrade organic polymers, such as, but not limited to, alkylphenol polyethoxylates, polyethylene glycol, dodecyl octylethoxylate, 1,4-dioxane, trioxane and cyclic ether, etc. Further, this strain can be grown in a culture medium containing alkylphenol polyethoxylates, utilizing alkylphenol polyethoxylates as a sole carbon source. In greater detail, this strain can degrade alkylphenol polyethoxylates, utilizing alkylphenol polyethoxylates as a sole carbon source, between 15 and 37 degrees Celsius and in an aerobic environment. The chemical formula of various alkylphenol polyethoxylates can be shown as follows:

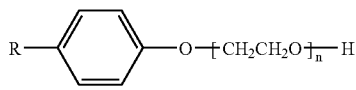

wherein, if R is an octyl group as shown below,

R:

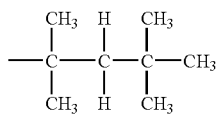

the alkylphenol polyethoxylates are octylphenol polyethoxylates (OPEOn) and if R is a nonyl group (branched chain or straight chain) as shown below, either branched:

R:

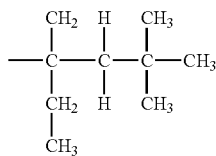

or straight:

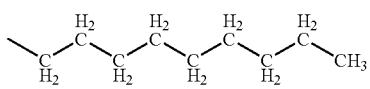

the alkylphenol polyethoxylates are nonylphenol polyethoxylate.

Particularly, this strain can be grown in a culture medium with a wide concentration range of alkylphenol polyethoxylates (0.05% to 20%). It is worth noting that the bacterial strain of the invention is able to grow well even in a culture medium with a very high concentration alkylphenol polyethoxylates.

In one aspect of the invention, when the bacterial strain of the invention is grown on a MSB (mineral salts basal) medium containing alkylphenol polyethoxylates, for example, 0.5%, the generation time is between 0.5 to 2 hours. Details on the MSB medium can be found in the publication, R. Y. G. Stanier, C. Bazire, and W. R. Sistrom, Kinetics studies of pigment synthesis by non-surfur purple bacteria. *J. Cell Comp. Physiol.,* 49: 25–28 (1966).

Figure 3:
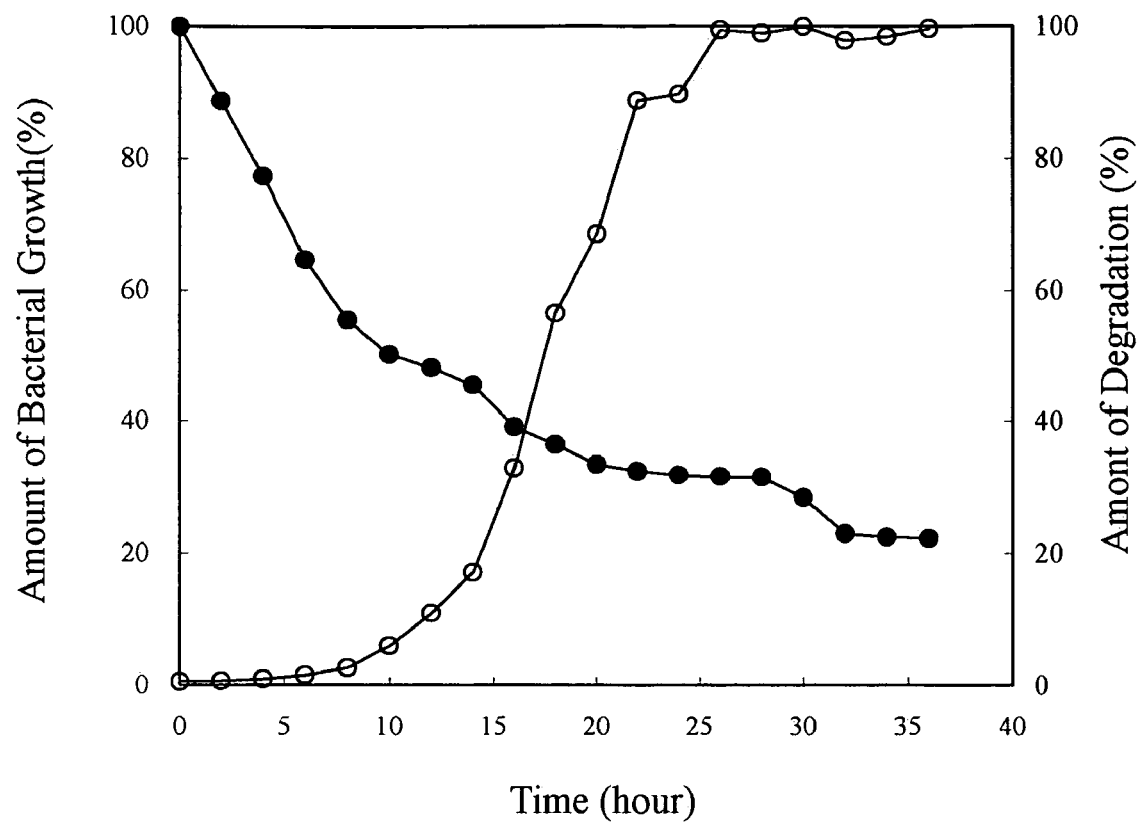
FIG. 3 is a diagram illustrating the growth rate and the degradation rate of the bacterial strain of the present invention grown in a culture medium containing octylphenol polyethoxylates as a sole source of carbon.

Further using octylphenol polyethoxylates as an example, FIG. 3 is a diagram illustrating the growth rate and the degradation rate of this strain in a culture medium containing octylphenol polyethoxylates as a sole source of carbon. As shown in FIG. 3, the x-axis represents time, the left y-axis represents the percentage of bacterial growth, and the right y-axis respects the percentage of octylphenol polyethoxylates degradation, with the percentage of bacterial growth is based on the largest amount of the bacteria that is generated (which is 100%). As clearly shown in FIG. 3, this bacterial strain can degrade octylphenol polyethoxylates, while the strain continues to grow.

Further, the oxygen uptake activity of this strain in degrading alkylphenol polyethoxylates is very high. The results of analysis indicate that the oxygen uptake over various different concentrations of alkylphenol polyethoxylates ranges from 230 μmole/min to 1000 μmole/min per gram of cell wet weight. This is the highest recorded oxygen uptake activity for alkylphenol polyethoxylates ever being reported.

Based on the foregoing, the bacterial strain of the invention can neutralize the activity of nonionic surfactants and degrade organic polymers. Further, this strain can be grown utilizing the nonionic surfactants or organic polymers as sole source of carbon. Therefore, the bacterial strain of the present invention is valuable for the treatment of environmental pollution, including the bioremediation of soils, the treatment of water contamination, and other similar systems.

It will be apparent to those skilled in the art that various modifications and variations can be made to the structure of the present invention without departing from the scope or spirit of the invention. In view of the foregoing, it is intended that the present invention cover modifications and variations of this invention provided, which fall within the scope of the following claims and their equivalents.

---

What is claimed is:

1. A biologically pure culture of bacterial strain *Pseuodomonas nitroreducens* TX1 (ATCC PTA-6168), which is capable of degrading organic polymers.

2. The culture of claim 1, wherein the bacterial strain is Gram-negative, rod-shaped and has the 16S ribosomal DNA sequence of SEQ ID NO. 1.

3. The culture of claim 1, wherein the bacterial strain is able to grow utilizing organic polymers as a sole carbon source, at temperatures ranging from 15 degrees Celsius to 37 degrees Celsius under aerobic growth conditions.

4. The culture of claim 3, wherein the bacterial strain is capable of degrading the organic polymers, wherein the organic polymers are selected from the group consisting of alkylphenol polyethoxylates, polyethylene glycol, dodecyl octylethoxylate, 1,4-dioxane, trioxane, and cyclic ether.

5. The culture of claim 1, wherein the bacterial strain is able to grow in an alkylphenol polyethoxylate-containing culture medium and where the bacterial strain degrades the alkylphenol polyethoxylates utilizing the alkylphenol polyethoxylates as a sole carbon source.

6. The culture of claim 5, wherein the generation time of the bacterial strain in the alklyphenol polyethoxylate-containing culture medium is from 0.5 to 2 hours.

7. The culture of claim 5, wherein the oxygen uptake activity of the bacterial strain using the alkylphenol polyethoxylates as substrate ranges from 230 to 1000 umol/min per gram of cell wet weight.

8. The culture of claim 5, wherein the alkylphenol polyethoxylates is selected from the group consisting of nonylphenol polyethoxylates, octylphenol polyethoxylates, and combinations thereof.

9. The culture of claim 5, wherein the bacterial strain degrades the alkylphenol polyethoxylates, wherein the alkylphenol polyethoxylates have the following formula:

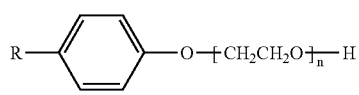

wherein R is an octyl group, and wherein the average n=9.5.

* * * * *

SEQUENCE LISTING

<160> NUMBER OF SEQ ID NOS: 1

<210> SEQ ID NO 1
<211> LENGTH: 1420
<212> TYPE: DNA
<213> ORGANISM: Pseudomonas sp.

<400> SEQUENCE: 1
ggcctaacca tgcaagtcga gcggatgagt ggagcttgct ccatgattca gcggcggacg    60

-continued

```
ggtgagtaat gcctaggaat ctgcctggta gtggggggaca acgtttcgaa aggaacgcta      120
ataccgcata cgtcctacgg gagaaagcag gggaccttcg ggccttgcgc tatcagatga      180
gcctaggtcg gattagctag ttggtggggt aaaggcctac caaggcgacg atccgtaact      240
ggtctgagag gatgatcagt cacactggaa ctgagacacg gtccagactc ctacgggagg      300
cagcagtggg gaatattgga caatgggcga aagcctgatc cagccatgcc gcgtgtgtga      360
agaaggtctt cggattgtaa agcactttaa gttgggagga agggcagtaa gttaatacct      420
tgctgttttg acgttaccaa cagaataagc accggctaac ttcgtgccag cagccgcggt      480
aatacgaagg gtgcaagcgt taatcggaat tactgggcgt aaagcgcgcg taggtggttt      540
ggtaagatgg atgtgaaatc cccgggctca acctgggaac tgcatccata actgcctgac      600
tagagtacgg tagagggtgg tggaatttcc tgtgtagcgg tgaaatgcgt agatatagga      660
aggaacacca gtggcgaagg cgaccacctg gactgatact gacactgagg tgcgaaagcg      720
tggggagcaa acaggattag ataccctggt agtccacgcc gtaaacgatg tcgactagcc      780
gttgggatcc ttgagatctt agtggcgcag ctaacgcgat aagtcgaccg cctggggagt      840
acggccgcaa ggttaaaact caaatgaatt gacgggggcc cgcacaagcg gtggagcatg      900
tggtttaatt cgaagcaacg cgaagaacct tacctggcct tgacatgtcc ggaaccttgc      960
agagatgcga gggtgccttc gggaatcgga acacaggtgc tgcatggctg tcgtcagctc     1020
gtgtcgtgag atgttgggtt aagtcccgta acgagcgcaa cccttgtcct tagttaccag     1080
cacctcgggt gggcactcta aggagactgc cggtgacaaa ccggaggaag gtggggatga     1140
cgtcaagtca tcatggccct tacggccagg gctacacacg tgctacaatg gtcggtacag     1200
agggttgcca agccgcgagg tggagctaat cccataaaac cgatcgtagt ccggatcgca     1260
gtctgcaact cgactgcgtg aagtcggaat cgctagtaat cgtgaatcag aatgtcacgg     1320
tgaatacgtt cccgggcctt gtacacaccg cccgtcacac catgggagtg ggttgctcca     1380
gaagtagcta gtctaaccgc aagggggacg gtaccacgga                           1420
```